United States Patent
Gill (10) Patent No.: US 10,130,814 B2
(45) Date of Patent: Nov. 20, 2018

(54) MOVEMENT DISORDER

(71) Applicant: RENISHAW PLC, Gloucestershire (GB)

(72) Inventor: Steven Gill, Gloucestershire (GB)

(73) Assignee: RENISHAW PLC, Wotton-Under-Edge (GB)

( * ) Notice: Subject to any disclaimer, the term of this patent is extended or adjusted under 35 U.S.C. 154(b) by 19 days.

(21) Appl. No.: 15/095,722

(22) Filed: Apr. 11, 2016

(65) Prior Publication Data

US 2016/0331971 A1    Nov. 17, 2016

(30) Foreign Application Priority Data

Apr. 9, 2015  (GB) .................................. 1506052.8

(51) Int. Cl.
*A61N 1/05*  (2006.01)
*A61N 1/36*  (2006.01)

(52) U.S. Cl.
CPC ..... *A61N 1/36067* (2013.01); *A61N 1/36185* (2013.01); *A61N 1/0534* (2013.01)

(58) Field of Classification Search
CPC .......................... A61N 1/36067; A61N 1/0534
See application file for complete search history.

(56) References Cited

U.S. PATENT DOCUMENTS

| | | |
|---|---|---|
| 5,935,795 A | 8/1999 | Lin et al. |
| 6,042,579 A | 3/2000 | Elsberry et al. |
| 6,348,050 B1 | 2/2002 | Hartlaub |
| 6,609,020 B2 | 8/2003 | Gill |
| 7,974,696 B1 * | 7/2011 | DiLorenzo ........... A61B 5/0476 607/2 |
| 2003/0203844 A1 | 10/2003 | Delfani et al. |
| 2007/0161919 A1 | 7/2007 | DiLorenzo |
| 2009/0011980 A1 | 1/2009 | Gill |
| 2009/0222067 A1 * | 9/2009 | Toselli ................ A61N 5/0601 607/88 |
| 2017/0143966 A1 * | 5/2017 | Reymers ............ A61N 1/36082 |

FOREIGN PATENT DOCUMENTS

| | | |
|---|---|---|
| WO | 03/077785 A1 | 9/2003 |
| WO | 2008/062173 A1 | 5/2008 |
| WO | 2008/098769 A1 | 8/2008 |

(Continued)

OTHER PUBLICATIONS

Bejjani et al., "Bilateral subthalamic stimulation for Parkinson's disease by using three-dimensional stereotactic magnetic resonance imaging and electrophysiological guidance", J Neurosurg 92:615-625, Apr. 2000.*

(Continued)

*Primary Examiner* — George Evanisko
(74) *Attorney, Agent, or Firm* — Oliff PLC (57) ABSTRACT

A method of treating a movement disorder using deep brain stimulation, the method comprising the step of inserting a lead having at least one electrode into the brain of a subject, the lead being inserted along a trajectory from the occipito-temporal or occipito-parietal regions, passing laterally to the posterior horn of the lateral ventricle to contact the subthalamic nucleus, the zona incerta or the globus pallidus.

11 Claims, 6 Drawing Sheets

(56) References Cited

FOREIGN PATENT DOCUMENTS

WO 2014/016591 A1 1/2014

OTHER PUBLICATIONS

Murata et al., "Electrical stimulation of the posterior subthalamic area for the treatment of intractable proximal tremor", J. Neurosurg., vol. 99, Oct. 2003, pp. 708-715.

Anderson et al., "Convection enhanced delivery of topotecan into diffuse intrinsic brainstem tumors in children", J Neurosurg Pediatrics 11, pp. 289-295, 2013.

Barua et al., "Robot-guided convection-enhanced delivery of carboplatin for advanced brainstem glioma", Acta Neurochir, 7 pages, 2013.

Brady et al., "Pathways of Infusate Loss During Convection Enhanced Delivery into the Putamen Nucleus", Stereotact Funct Neurosurg. 20134 91(2), pp. 69-78, 2013.

Chen et al., "Variables affecting convection-enhanced delivery to the striatum; a systematic examination of rate of infusion, cannula size, infusate concentration, and tissue-cannula sealing time", J Neurosurg 90, pp. 315-320, 1999.

Freed et al., "Transplantation of embryonic dopamine neurons for severe Parkinson's disease", The New England Journal of Medicine, vol. 344, No. 10, pp. 710-719, 2001.

Gill et al., "Direct brain infusion of glial cell line-derived neurotrophic factor in Parkinson disease", Nature Medicine, pp. 1-7, 2003.

Rosenblad et al., "Sequential Administration of GDNF into the Substantia Nigra and Striatum Promotes Dopamine Neuron Survival and Axonal Sprouting but Not Striatal Reinnervation or Functional Recovery in the Partial 6-OHDA Lesion Model", Experimental Neurology, 161, pp. 503-516, 1999.

Slevin et al., "Improvement of bilateral motor functions in patients with Parkinson disease through the unilateral intraputaminal infusion of glial cell line-derived neurotrophic factor", J Neurosurg, 102, pp. 216-222, 2005.

Aug. 16, 2017 Office Action issued in U.S. Appl. No. 14/610,185.
Feb. 27, 2018 Office Action issued in U.S. Appl. No. 14/610,185.
U.S. Appl. No. 14/610,185, filed Jan. 30, 2015 in the name of Gill.

\* cited by examiner

MOVEMENT DISORDER

This application claims the benefit of priority to GB Application No. 1506052.8 filed Apr. 9, 2015. The entire disclosure of the prior application is hereby incorporated reference herein in its entirety.

TECHNICAL FIELD

This application is directed to improved neurosurgical methods for treating movement disorders.

BACKGROUND

Movement disorders refer to a number of conditions including Hypokinesia (Parkinson's disease), Hyperkinetic disorders (L-dopa induced dyskinesia, Hemiballism and Chorea), Dystonia (generalized and localized) and Tremor (Resting, Postural and Action tremor).

Parkinson's disease (PD) is a chronic, progressive neurodegenerative movement disorder. The main symptoms are tremors, rigidity, slow movement (bradykinesia), poor balance and difficulty walking. The highest prevalence of PD is in Europe and North America with around 1 to 1.5 million people being affected in the USA. Caucasian populations are affected more than others, with a prevalence of around 120-180 per 100,000 people. Symptoms of PD may appear at any age, but the average age of onset is 60. PD is rare in young people and risk increases with age. The cause of the disease is unknown, but there may be genetic factors.

PD is associated with degeneration of several neuronal modulators in the midbrain that primarily affect the motor system. These include the midbrain dopaminergic nuclei, the serotoninergic median raphe nuclei, the noradrenergic locus coeruleus and the cholinergic pedunculopontine nucleus.

At present, there is no cure for PD. Medical treatment for PD relies on a variety of drugs that stimulate dopamine receptors and although this approach may be effective for 5-10 years, therapy is complicated by motor side effects including "on/off" fluctuations and dyskinesias. With progressive degeneration of the dopaminergic system and other neuronal modulators the patient develops fluctuating responses to medical intervention. Surgery may be contemplated in patients who are poorly controlled on the best medical therapy.

Hyperkinetic disorders are sudden rapid involuntary and purposeless movements that typically intrude into the patient's normal activity. These movements may be both axial and peripheral. Examples of hyperkinetic disorders include L-Dopa dyskinesia, which is a complication of PD, Chorea and Hemiballism, which may result from brain lesions involving the basal ganglia. There are no effective medical treatments for these conditions.

Dystonia is a postural disorder characterized by involuntary muscle contractions affecting various parts of the body including the limbs, trunk, shoulders, face and neck.

Tremor is involuntary oscillatory movements produced by alternating contractions of agonist and antagonist muscles. These movements can affect the proximal and distal limb muscles and also the axial muscle groups. Tremor can occur at rest, with the limb maintained in a particular posture and/or during movements. Tremor can occur as a sign of PD, and as a result of lesions of the basal ganglia, midbrain or the cerebellum, but its most common form is familial Essential Tremor (ET). Medical treatments tend to variably suppress rather than abolish tremor.

At present there are various surgical treatments available for movement disorders; however, many of them involve side effects. Movement disorders are due to abnormal patterns of neuronal firing permeating the motor pathways. Surgical treatment aims to disrupt the transmission of these abnormal patterns by destroying or lesioning motor pathways or nuclei or alternatively overriding the abnormal patterns with high frequency electrical stimulation. The latter treatment is known as Deep Brain Stimulation (DBS) and is achieved by implanting an electrode into the pathways or nuclei in the brain and delivering pulsed electrical current to the tissue from an implanted pulse generator which is connected to the electrode.

A number of targets are known to be effective in the treatment of movement disorders. These include the Globus Pallidus Internus (Gpi), the Ventral Intermediate Nucleus (Vim) of the thalamus and the Subthalamic Nucleus (STN).

Lesions or DBS of the Gpi can be effective for the treatment of PD, Dystonia and Hyperkinetic movements. This type of treatment has a modest effect on PD symptoms such as tremor, rigidity, bradykinesia and akinesia, but is effective in treating the motor side effects of L-dopa therapy such as dyskinesia and dystonia which allow the patient to continue on a high dose of medication.

Bilateral Gpi lesions/DBS are associated with worsening axial symptoms including deterioration in speech, swallowing and gait.

The conventional method for placing stimulating or lesioning electrodes in subcortical targets for treating movement disorders involves 3 steps:

1/Identifying the target on radiological images of the patient's brain either directly, or indirectly with reference to a brain atlas.

2/Registering the spatial information on the image to an aiming instrument or stereoguide. This is conventionally done by fixing a frame to the patient's head that carries fiducials that can be visualised on the brain images and from which the stereoguide's Cartesian coordinate system can be determined. The coordinates of the target are then set in the stereoguide that in turn is fixed to the frame.

3/Implanting the electrode and confirming its location peri-operatively. Conventionally electrode placement is carried out through a frontal burr hole with the patient awake. Stimulation of the target site during the procedure confirms appropriate placement by inducing symptomatic movement. Target localisation can also be confirmed with microelectrode recording. Here micro-electrodes are passed through the region of interest in the brain until neuronal firing patterns characteristic of the target are recorded. In recent years some groups have been implanting DBS electrodes in anaesthetised patients and confirming accurate electrode placement with peri-operative imaging alone.

The conventional trans-frontal approach to functional neurosurgical targets has the disadvantage that the electrode trajectory (which is approximately 45 degrees to the anterior commissure (AC)—posterior commissure (PC) plane) is generally orthogonal to the elongate functional topography of the basal ganglia. This generally limits the field of stimulation to a small portion of the motor representation of the target nucleus so limiting the potential therapeutic benefit.

The constraints imposed by the established trans-frontal trajectory require the surgeon to select a location in the target nucleus that may best treat the most dominant features of the patient's disease. By way of example, the STN is one of the most frequently targeted structures for the treatment of Parkinson's disease with DB S and its dorso-caudal half is attributed with motor function. A surgeon wishing to treat a PD patient with akinesia as a dominant symptom may target the middle of the STN, at the junction of its motor and associative portions, but if treating a patient with tremor and rigidity then targeting the more posterior portions of the dorso-caudal nucleus would give better symptomatic control. However, patients with PD have variable and progressive symptoms and so it is difficult to target a single location along the rostro-caudal functional topography that will effectively control all symptoms.

Indeed, in addition to motor functions, the STN has limbic and associative functions. Disruption of these with DBS may contribute to worsening anxiety and depression seen with this treatment. Medial to the STN are fibers carrying cerebellar information to the thalamus and spread of current to these may interfere with information regarding precision movements of the larynx and hence cause worsening of speech. Stimulation of structures rostral and ventral to the subthalamic nucleus including the substantia nigra and area of Sano are associated with severe depression and mania/rage respectively.

Although bilateral simulation of the STN is currently regarded as the optimum target by many neurosurgical centers, the most effective therapeutic contact on a quadripolar DBS lead transfixing the STN has been reported as being one positioned at the interface of the dorsal surface of the STN and the adjacent white matter tracts.

Murata et al., describe stimulating the posterior subthalamic area for treating proximal tremor. The surgery utilised a conventional frontal burr hole approach. The treatment area selected by Murata et al. is particularly close to the prelemniscal radiation. Stimulation of this area can result in severe side effects such as speech disturbances, difficulty with precision movements and postural problems.

In view of the problems associated with DBS, there is a need for improved methods for treating movement disorders.

SUMMARY

In embodiments, there is provided a method of treating a movement disorder using deep brain stimulation, the method comprising inserting at least one lead into the brain of a subject along a trajectory from the occipito-temporal or occipito-parietal regions, passing laterally to the posterior horn of the lateral ventricle to contact a target area of the brain, the lead comprising at least one electrode; and electrically stimulating the target area of the brain through the electrode.

DETAILED DESCRIPTION

The basal ganglia comprise several elongate subcortical nuclei situated in the forebrain in a rostro/caudal orientation. They include the striatum, putamen, globus pallidus, nucleus accumbens, subthalamic nucleus and the substantia nigra. The basal ganglia are involved in the selection and facilitation of behavioural repertoires and their dysfunction is associated with behavioural and motor disorders. These disorders may be treated surgically by placing lesioning or stimulating electrodes in functionally relevant volumes in basal ganglia nuclei to modulate their output.

The topographical arrangement of the basal ganglia reflect cortical functional topography with volumes representing motivational aspects of behaviour (limbic) being represented rostro-ventrally, those representing motor function dorso-caudally with associative function being represented between these volumes.

Disclosed embodiments are directed to a method of treating a movement disorder using deep brain stimulation (DBS). The method comprises the step of inserting a lead having at least one electrode into the brain of a subject such as a patient, the lead being inserted along a trajectory from the occipito-temporal or occipito-parietal regions, passing laterally to the posterior horn of the lateral ventricle to contact the subthalamic nucleus, the zona incerta or the globus pallidus. Preferably the lead is a deep brain stimulation (DBS) lead. Leads may be inserted bilaterally into the brain.

Figure 1A:
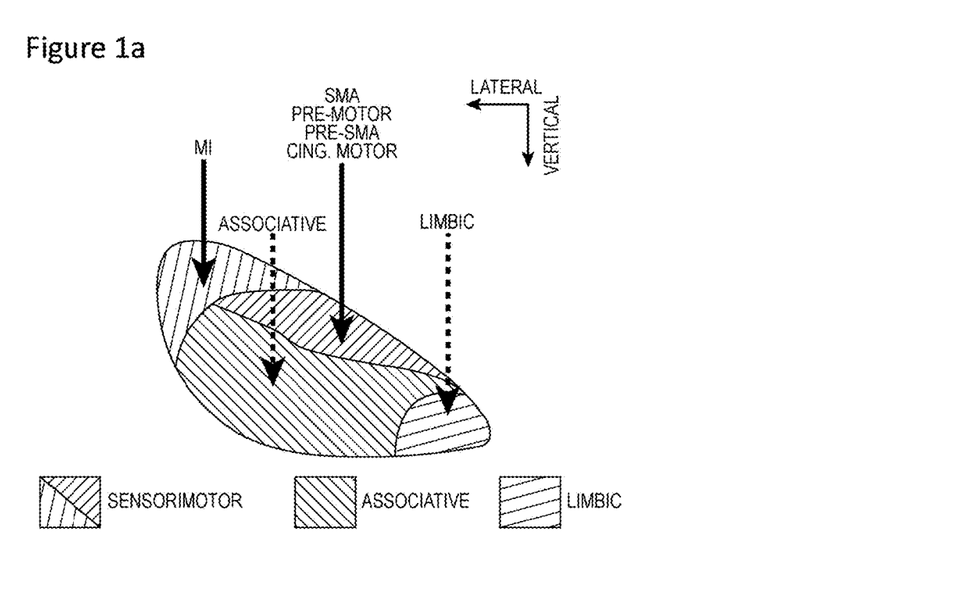
FIGS. 1a and 1b show schematic illustrations of the topography of the subthalamic nucleus.
Figure 1B:
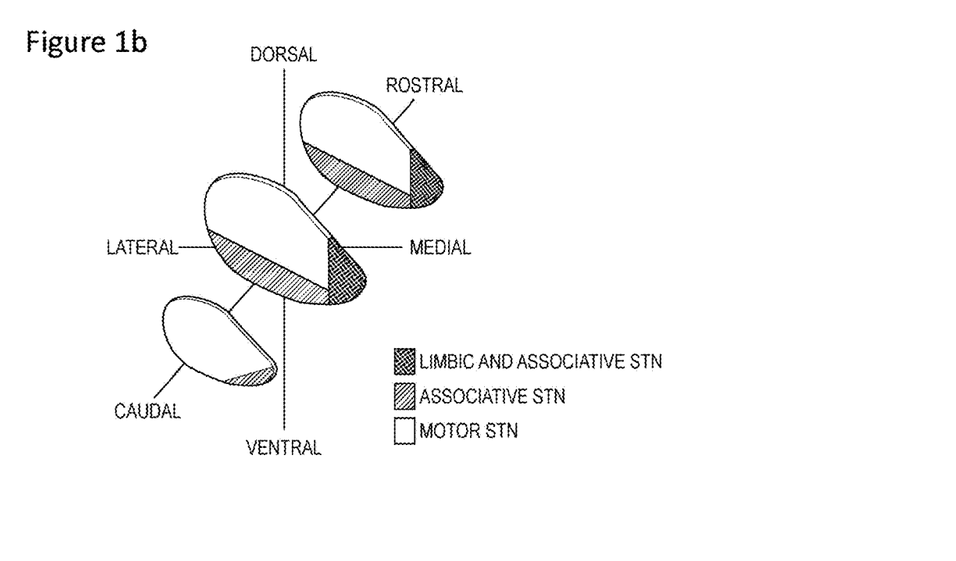
Figure 2:
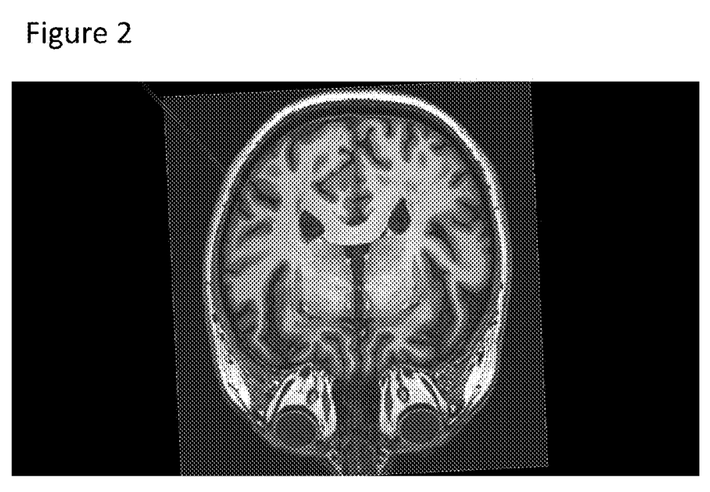
FIGS. 2-6 show images of the posterior approach to the subthalamic nucleus.
Figure 3:
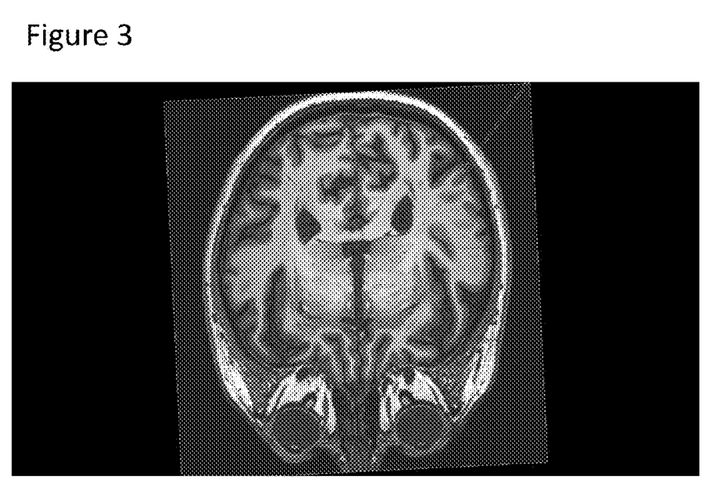
Figure 4:
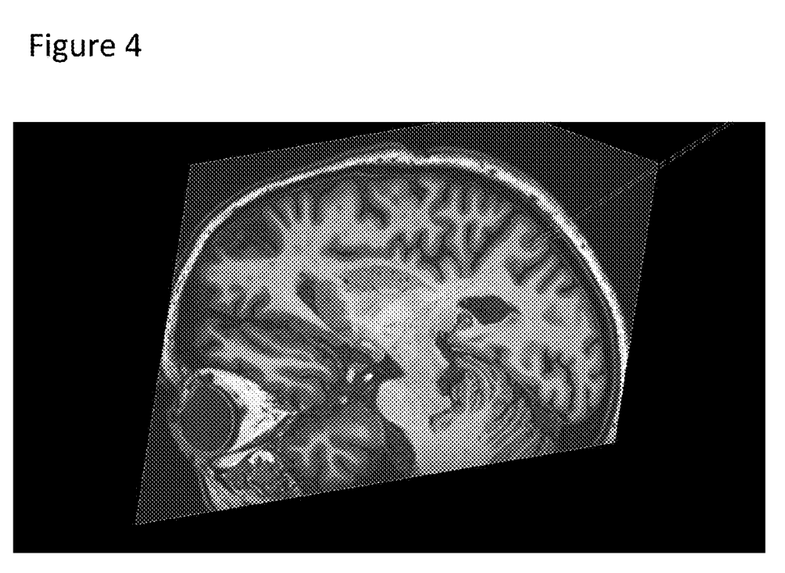
Figure 5:
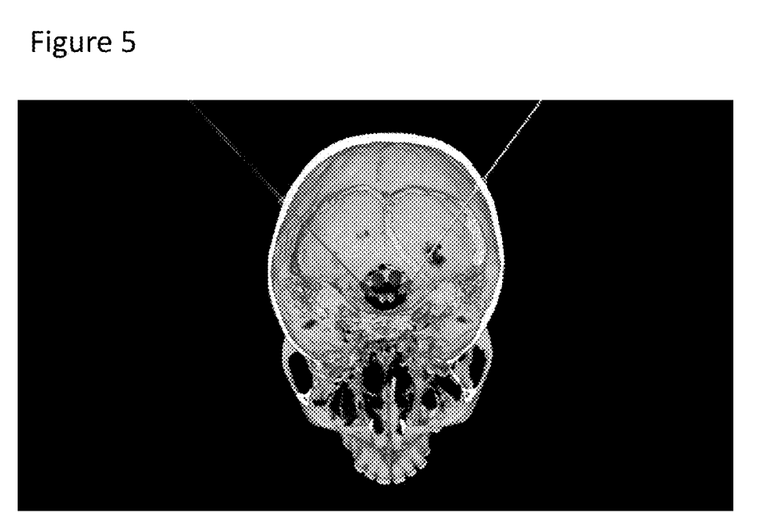
Figure 6:
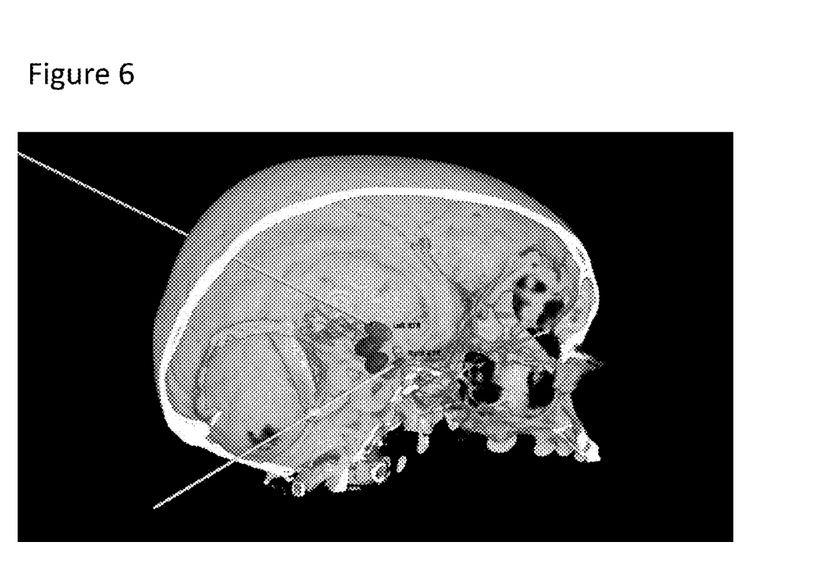
Figure 7:
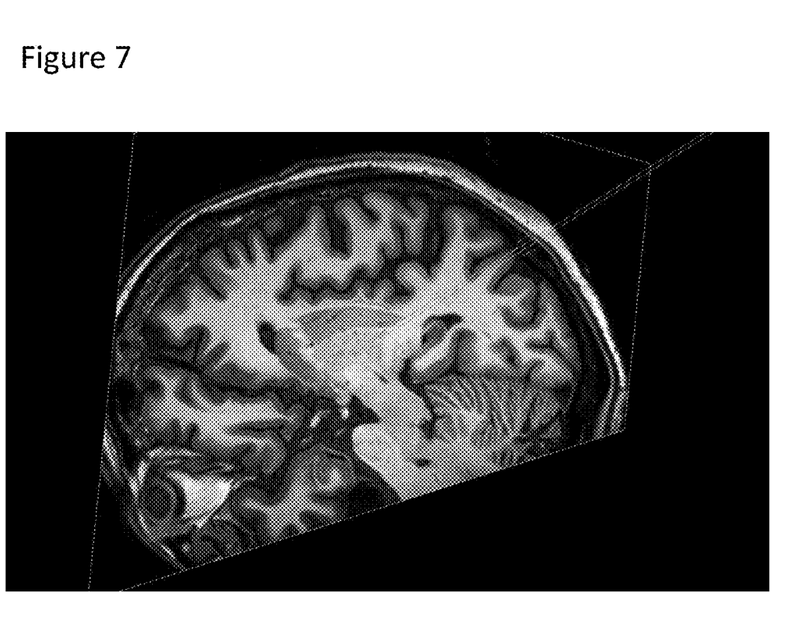
FIGS. 7-9 show images of the posterior approach to the globus pallidus interna.
Figure 8:
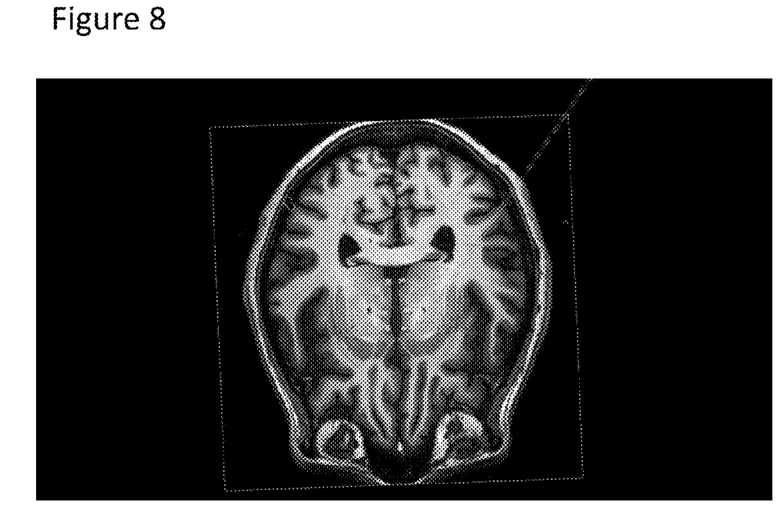
Figure 9:
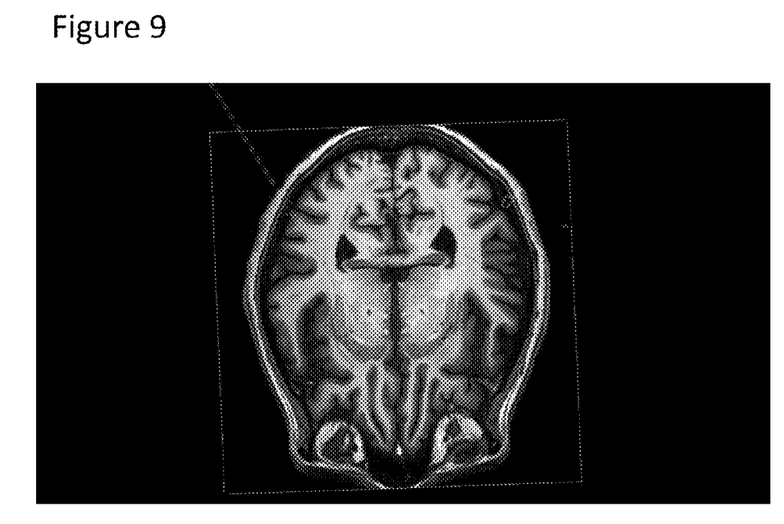

The lead trajectory facilitates the placement of several electrode contacts within or in contact with the nucleus such that each will stimulate a different portion of the functional topography in a rostro-medial to caudo-lateral orientation. The advantage of such a trajectory is that different elements of movement preparation and execution can be modulated by stimulating appropriately selected electrode contacts or combinations of contacts to optimise symptom control for individual patients. The topography of the subthalamic nucleus is illustrated schematically in FIG. 1. The zona incerta and globus pallidus have similar topographies.

The accuracy of targeting brain structures in functional neurosurgery through a conventional trans-frontal approach is typically in the range of +/−3 mm. Misplacement of an electrode from a selected target by 3 mm may result in poor symptomatic control or significant side effects. Inadvertent targeting of, for example, the rostral, limbic and/or associative regions of the STN, which are within 3 mm of the commonly targeted central portion, is associated with provoking depression, anxiety and impulsive behaviour. The posterior approach to the STN as described herein, in which an electrode lead is placed along its long axis, facilitates adjustment of the site of stimulation topographically, so that inadvertent stimulation of limbic or associative sites can be avoided by changing the activated contact to one that is more caudal. Preferably the lead contacts the dorso-medial region of the STN.

Targeting the globus pallidus, preferably the globus pallidus interna (GPi) through a posterior approach with a skull entry point through the posterior temporo-occipital region or the posterior parieto-occipital region also has advantages over the conventional trans-frontal approach. In this instance the trajectory also passes through the optic radiation, lateral to the posterior horn of the lateral ventricle and thence into the caudal GPi. The posterior approach facilitates placement of a lead with multiple electrode contacts along the rostro-caudally arranged functional topography. For the optimal treatment of generalised dystonia it is desirable to stimulate the greater part of the motor representation of the GPi which may occupy the caudal half of the GPi. This would be difficult to achieve with a frontal trajectory that is orthogonal to the rostro-caudal orientation of the nucleus. Treatment of focal dystonia can be optimised by selecting between several electrode contacts in the motor GPi and for the treatment of Tourette's Syndrome the posterior trajectory also facilitates simultaneous stimulation of contacts in the motor and associative regions of the GPi through a single lead.

Preferably the posterior insertion trajectory is aligned substantially with the long (caudo-rostral) axis of the subthalamic nucleus, the zona incerta or the globus pallidus, for example, to within the range of 30° or less of the long (caudo-rostral) axis of the subthalamic nucleus, the zona incerta or the globus pallidus.

As mentioned above, an advantage of the disclosed method is that multiple electrode contacts on a single lead can be placed in contact with the target structure. For example, at least two, or at least 3, or at least 4 or more electrodes on a lead can be placed in contact with the subthalamic nucleus, the zona incerta or the globus pallidus, preferably along their rostro-caudal axes. Following surgical placement of the electrodes, patients are seen by a medical professional for "programming". During this procedure (usually carried out once post-surgical inflammation has subsided) the electrodes are individually adjusted to determine the effect on the patient's symptoms. Adjusting the electrical current to different electrodes can optimise the treatment effect. A particular advantage of the disclosed method is that the placement of the lead along the long axis of the target structure allows a greater number of the electrodes to be placed in contact with a greater volume of the target structure. Consequently, it is possible to have finer control over stimulation of areas of the target structure than has previously been possible.

Movement disorders treated according to embodiments can include one or more of Parkinson's disease, Huntington's disease, dystonia, tremor or Tourette's syndrome.

The posterior to anterior insertion trajectory allows the disclosed method to be carried out on a subject such as a patient under general anaesthetic and in a prone position. Movement of the brain during neurosurgery can be a particular problem as even a few millimeters of displacement can significantly affect the accuracy of an implement inserted into the brain. Not only will the brain move if and when the patient is moved, but the action of inserting an implement can itself displace the brain in the direction of the insertion. The prone position of the patient in the disclosed methods can have advantages, as when the patient is turned from their back onto their front the brain displaces anteriorly in the skull. The lead insertion is then from the posterior toward the anterior, however, as the brain has already displaced anteriorly any further displacement due to lead insertion is likely to be minimal. The position of the brain target with the patient in the prone position can be determined from radiological imaging of the patient in this position and registering this with a coordinate system of a surgical aiming device. The disclosed methods can therefore provide highly accurate targeting of structures in the brain. In preferred embodiments, the patient may be a human.

EXAMPLES

Electrodes were placed into the subthalamic nucleus and zona incerta to treat Parkinson's disease and tremor (Essential tremor, dystonic tremor, Holmes tremor and cerebellar tremor in multiple sclerosis). The globus pallidus interna was targeted to treat dystonia, Tourette's syndrome and Huntington's disease. These are all preferentially treated using a posterior trajectory. The surgical approach employs an implantable plastic guide tube that is inserted along the trajectory and is retained by a proximal hub that is press-fitted into the skull and through which the DBS electrode lead is inserted to the target.

The surgical procedure begins with the acquisition of high resolution MRI images of the patient's brain. From these image volumes the target and trajectory are planned with the assistance of surgical planning software (Neuroinspire, Renishaw plc).

The anaesthetised patient has a stereotactic frame (Leksell frame) fixed to the head and the patient is placed in a prone position and the stereotactic frame is fixed to a robot stand (Neuromate robot, Renishaw plc). The patient is now registered to the surgical plan and to the surgical robot. This is achieved by using an intra-operative CT scanner (O-arm, Medtronic Inc.) and acquiring a CT angiogram of the patients head whilst the robot arm holds a reference fiducial in the CT scanner's field of view. The blood vessels identified on the CT angiogram are registered to the vessels seen on the planning MRI scan using a matching algorithm in the software. This provides a highly accurate registration of the plan to the patient and the relationship between the robot arm and the patient is established from the fiducials held by the robotic arm that are also visualised on the CT angiogram.

After preparing and draping the surgical site an incision is made over the temporo-occipital region or the parieto-occipital region and the skull is exposed. The robot is positioned to guide instruments along the pre-defined trajectory and a 1.8 mm drill hole is made through the skull and dura. A profile drill is now used to create a datum 1 mm below the skull surface and a press-fit profile in the skull to retain the guide tube's hub in a predetermined position. The guide tube is cut to length, typically 10 mm short of the datum to target distance, and delivered to target over a probe such that its hub is press-fitted into the skull. The probe is removed and replaced with a plastic radio-opaque stylette that projects 10 mm beyond the distal end of the guide tube to reach the target.

The targeting accuracy is verified by repeating the head CT angiogram with the guide tube(s) and stylette(s) in situ and fusing this image with the pre-operative plan. If the targeting accuracy is satisfactory then the stylette is withdrawn and replaced with an electrode lead that is inserted to the same depth.

The mean targeting accuracy of DBS lead placement using the posterior trajectory and this technique is generally within 0.5 mm. It was unexpectedly found that the posterior trajectory is advantageous when compared to the conventional frontal trajectory with regard to targeting accuracy. When passing an instrument through the brain to a deep subcortical target from a frontal approach, approximately 45 degrees to the AC/PC plane, the brain is displaced posteriorly, inferiorly and laterally to a variable extent depending on the respective A/P and lateral angles of approach. With the patient in a prone position as described for a posterior approach, the brain shifts anteriorly and is relatively fixed when the probe is inserted in a predominantly posterio-anterior direction approximately parallel to the AC/PC plane. This limits the potential vector and magnitude of displacement. This enhanced accuracy increases the safety and efficacy of the procedure.

It will be appreciated that the above-disclosed features and functions, or alternatives thereof, may be desirably combined into different systems or methods. Also, various alternatives, modifications, variations or improvements may be subsequently made by those skilled in the art, and are also intended to be encompassed by the following claims. As such, various changes may be made without departing from the spirit and scope of this disclosure as defined in the claims.

REFERENCES

Murata J, Kitagawa, M, Uesugi H, Saito H, Iwasaki Y, Kikuchi S, Tashiro K, Sawamura Y. Electrical stimulation of the proximal subthalamic area for the treatment of intractable proximal tremor. J. Neurosurg 2003; 99: 708-715.

The invention claimed is:

1. A method of treating a movement disorder using deep brain stimulation, the method comprising:
    inserting at least one lead into the brain of a subject along a trajectory from the occipito-temporal or occipito-parietal regions, passing laterally to the posterior horn of the lateral ventricle to contact a target area of the brain, the lead comprising at least one electrode; and
    electrically stimulating the target area of the brain through the electrode,
    wherein the target area of the brain is selected from the group consisting of the subthalamic nucleus, the zona incerta and the globus pallidus.

2. The method according to claim 1, wherein the insertion trajectory is aligned substantially with the long (caudo-rostral) axis of the subthalamic nucleus, the zona incerta or the globus pallidus.

3. The method according to claim 2, wherein the insertion trajectory is aligned to within the range of 30° or less of the long (caudo-rostral) axis of the subthalamic nucleus, the zona incerta or the globus pallidus.

4. The method according to claim 1, wherein the lead comprises at least two electrodes, the at least two electrodes are placed in contact with the target area of the brain.

5. The method according to claim 4, wherein the lead comprises four or more electrodes, the four or more electrodes are placed in contact with the subthalamic nucleus, the zona incerta or the globus pallidus.

6. The method according to claim 4, further comprising modulating the treatment by selectively stimulating electrodes in contact with the target area of the brain.

7. The method according to claim 1, wherein the movement disorder is selected from the group consisting of Parkinson's disease, Huntington's disease, dystonia, tremor and Tourette's syndrome.

8. The method according to claim 1, wherein the lead is inserted while the subject is under general anaesthetic.

9. The method according to claim 8, wherein the subject is in a prone position.

10. The method according to claim 1, further comprising inserting at least a second lead into the brain of the subject, wherein the leads are inserted bilaterally into the target area of the brain.

11. The method according to claim 1, wherein the subject is a human.

* * * * *